(12) United States Patent
Pestman et al.

(10) Patent No.: US 6,452,002 B2
(45) Date of Patent: Sep. 17, 2002

(54) PROCESS TO CONTINUOUSLY PREPARE AN AQUEOUS MIXTURE OF ε-CAPROLACTAM AND ε-CAPROLACTAM PRECURSORS

(75) Inventors: Robert Pestman, Eindhoven; Lambertus H. W. M. Van Lieshout, Ulestraten, both of (NL)

(73) Assignees: DSM N.V., Heerlen (NL); E.I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 09/795,706

(22) Filed: Mar. 1, 2001

Related U.S. Application Data

(63) Continuation-in-part of application No. PCT/NL99/00544, filed on Sep. 1, 1999.
(60) Provisional application No. 60/100,404, filed on Sep. 1, 1999.

(30) Foreign Application Priority Data

Sep. 3, 1998 (EP) .............................. 98202943

(51) Int. Cl.$^7$ ............................................ C07D 201/08
(52) U.S. Cl. .................................................... 540/538
(58) Field of Search ........................................ 540/538

(56) References Cited

U.S. PATENT DOCUMENTS

| | | | |
|---|---|---|---|
| 4,730,040 A | 3/1988 | Vagt et al. .................. | 540/538 |
| 4,766,237 A * | 8/1988 | Hutmacher et al. .......... | 560/155 |
| 5,652,362 A | 7/1997 | Kuo et al. ................... | 540/538 |
| 5,700,934 A | 12/1997 | Wolters et al. .............. | 540/538 |
| 5,717,089 A * | 2/1998 | Wolters et al. .............. | 540/538 |
| 5,877,314 A | 3/1999 | Herkes et al. .............. | 540/538 |
| 5,977,356 A * | 11/1999 | Chu et al. .................... | 540/538 |

FOREIGN PATENT DOCUMENTS

| | | |
|---|---|---|
| DE | 3602377 A1 | 7/1987 |
| EP | 0 150 295 | 8/1985 |
| EP | 0 729 943 A | 9/1996 |
| EP | 0 729 944 | 9/1996 |
| JP | 47 027984 | 2/1971 |
| JP | 62 169769 | 7/1987 |
| WO | WO 98/09944 * | 3/1998 |

* cited by examiner

Primary Examiner—Bruck Kifle
(74) Attorney, Agent, or Firm—Pillsbury Winthrop LLP

(57) ABSTRACT

Process for preparing an aqueous mixture of ε-caprolactam and 6-aminocaproic acid and/or 6-aminocaproamide which involves, as the reductive amination step, contacting 5-formylvaleric acid and/or an alkyl 5-formylvalerate in water as solvent with hydrogen and an excess of ammonia in the presence of a ruthenium on carrier, as a catalyst, wherein the carrier is titanium oxide, zirconium oxide, graphite or carbon and the catalyst also contains at least one of the metals of group 8-11, or a compound of these metals. The aqueous mixture can be used to prepare ε-caprolactam.

13 Claims, No Drawings

PROCESS TO CONTINUOUSLY PREPARE AN AQUEOUS MIXTURE OF ε-CAPROLACTAM AND ε-CAPROLACTAM PRECURSORS

This application is a continuation-in-part of international application No. PCT/NL99/00544, filed Sep. 1, 1999, which designated the U.S., and was published under PCT Article 21(2) in English, and also claims the benefit of priority of U.S. provisional application No. 60/100,404, filed Sep. 1, 1999.

The invention relates to a process for preparing an aqueous mixture of ε-caprolactam and 6-aminocaproic acid and/or 6-aminocaproamide by reductively aminating 5-formylvaleric acid and/or an alkyl 5-formylvalerate in water with hydrogen and an excess of ammonia in the presence of a ruthenium on carrier catalyst.

A process for preparing ε-caprolactam is described in U.S. Pat. No. 4,730,040. In this process, methyl 5-formylvalerate is first hydrolyzed (step a) in the presence of water and an acidic agent to yield 5-formylvaleric acid. In this process, the 5-formylvaleric acid is reductively aminated in water through contact with ammonia and hydrogen using a ruthenium/zirconium on alumina catalyst, a Raney Nickel catalyst or a Raney Cobalt catalyst to obtain a 6-aminocaproic acid containing reaction mixture. After separation of ammonia, the reaction mixture obtained from the reductive amination is heated to 300° C. to form ε-caprolactam by cyclization of the 6-aminocaproic acid.

A disadvantage of the process according to U.S. Pat. No. 4,730,040 is the poor yields obtained from the reductive amination which prevent it from being a commercially attractive process. According to the experimental results, the best yield of the hydrolysis step is only about 78%, the best yield of the reductive amination step is only about 77% and the best yield of the final step is only about 95%. Hence, the overall yield is at most 57%.

Another disadvantage is that when the reductive amination is performed for a prolonged period of time, a decrease in particle size of the Raney Nickel and alumina catalyst particles has been found to occur. This is not desired because these small particles may disturb any filtration operation or lead to catalyst losses due to entrainment of the catalyst in the product stream.

A further disadvantage of this process is that the initial activity of the catalyst system is relatively small.

A still further disadvantage is that after some hours of continuous operation the activity of the catalyst can decrease.

An object of the present invention is to reproducibly obtain a higher yield to ε-caprolactam and ε-caprolactam precursors (6-aminocaproic acid and 6-aminocaproamide) in the reductive amination with an improved initial catalyst activity without suffering the above described problems, including the decrease of the catalyst particle size or loss of catalyst activity.

This object is achieved in that the carrier is titanium oxide, zirconium oxide, graphite or carbon and the catalyst also contains at least one of the metals of group 8-11, or a compound of these metals.

It has been found that when the process according to the invention is performed a high yield to ε-caprolactam and ε-caprolactam precursors can be achieved in the reductive amination, and the catalyst retains its particle size and activity over a prolonged period of time. Another advantage is that the initial activity of the catalyst system is improved. Another advantage is that the selectivity of ε-caprolactam precursors is also improved. Another advantage is that when starting from an alkyl 5-formylvalerate a separate hydrolysis step in order to prepare 5-formylvaleric acid, such as described in U.S. Pat. No. 4,730,040, is not needed. This is very advantageous because the separate hydrolysis of the alkyl 5-formylvalerate as described in U.S. Pat. No. 4,730,040 showed a low yield (78%) to 5-formylvaleric acid. It has been found that the alkyl 5-formylvalerate can be directly used in the present process, resulting in a high yield to ε-caprolactam while avoiding the low-yield-hydrolysis step described in U.S. Pat. No. 4,730,040.

According to EP-A-729943 and EP-A-729944 ε-caprolactam can be prepared by first contacting methyl 5-formylvalerate with ammonia and subsequently reacting the intermediate compounds thus formed, probably imine-caproic acid derivatives, with hydrogen in the presence of ammonia and, for example, a ruthenium on alumina catalyst or Raney Nickel. These patent applications mention copper, iron and/or chrome as possible additional metal in addition to nickel, cobalt or ruthenium on alumina, silica, titanium oxide, magnesium oxide, zirconium oxide or carbon as possible carrier material. However, only ruthenium on alumina carriers containing no substantial amount of a further metal are used in the examples of EP-A-729943 and EP-A-729944. However when using the exemplified ruthenium on alumina catalyst the earlier mentioned problem of particle size reduction also takes place. It was therefore not expected that by using a ruthenium and at least one further group 8-11 metal on zirconium oxide, titanium oxide, graphite or carbon carrier in a one-step reductive amination that a high yield to ε-caprolactam precursors and a high initial catalytic acitiviy could be achieved while at the same time avoiding loss of catalyst activity and reduction of catalyst particle size.

According to the publication WO-A-9835938 ε-caprolactam and ε-caprolactam precursors are prepared in water starting from methyl 5-formylvalerate in the presence of ruthenium on titanium oxide or zirconium oxide as catalyst. The use of a group 8-11 metal as further catalyst component is not disclosed or suggested.

The catalysts used in the process of the present invention are combinations of ruthenium and at least one further group 8-11 metal or compounds thereof, on a carrier selected from titanium oxide, zirconium oxide, graphite or carbon. Of the further group 8-11 metal Co, Rh, Ir, Ni, Pd, Pt and Cu are preferred. The most preferred further group 8-11 metal is Rh and Ni.

The carrier is titanium oxide, zirconium oxide, graphite or carbon. Titanium oxide and zirconium oxide are preferably used as the carrier because of its high chemical and mechanical stability and because the selectivity to the preferred (intermediate) compounds is found to be relatively high when these supports are used.

A relatively small but catalytically effective amount of the catalyst is used in the present process. The amount of ruthenium (as metal) in the catalyst (metal plus carrier) is generally between 0.1 and 10 wt %. The amount of the group 8-11 metal (as metal) in the catalyst (metals plus carrier) is generally between 0.05 and 30 wt. %, preferably between 0.1 and 10 wt. % and more preferably between 0.1 and 5 wt. %. The molar ratio of ruthenium to the other metal is generally within the range from 100:1 to 1:10, preferably from 20:1 to 1:1. The mean particle size ($d_{50}$) of the catalyst is preferably between 10 and 100 μm, when the catalyst is present as a slurry in the reaction mixture or between 0.001 and 0.05 m, when the catalyst is present in a fixed bed. The BET surface area can be between 1 and 100 m$^2$/g. The BET surface area is preferably between 30 and 100 m$^2$/g. Preferably anatase is used as carrier to reach such a high BET surface area of titanium oxide. The high BET surface area is advantageous because higher catalyst activity can be obtained.

The catalyst can be prepared by any of the processes known for a man skilled in the art. The supported catalyst is suitably prepared by adding at least one group 8-11 metal salt to a ruthenium on carrier and subsequently precipitation of the group 8-11 metal salt by means of evaporation the solvent, so called impregnation or by means of reduction of the catalyst. Another suitable method for preparing the catalyst is adding a group 8-11 metal salt to a ruthenium on carrier and subsequently precipitation of the group 8-11 metal salt by means of adjustment of the pH of the solution.

The alkyl 5-formylvalerate compound is preferably a $C_1$–$C_6$ alkyl 5-formylvalerate compound. Examples of suitable alkyl groups are methyl, ethyl, propyl, iso-propyl, tert-butyl, n-butyl, iso-butyl, cyclohexyl. More preferably methyl and ethyl groups are used because methyl- and ethyl-5-formylvalerate are readily obtainable such as, for example, by the processes described in U.S. Pat. No. 5,527,950, WO-A-9404482 and WO-A-9506025. A method for preparing 5-formylvaleric acid starting from a pentenoic acid is, for example, described in WO-A-9518783. Preferably the starting compound is an alkyl 5-formylvalerate because these compounds are more readily available than 5-formylvaleric acid. Unless otherwise stated, reference herein to the formyl-starting compound means alkyl 5-formylvalerate, 5-formylvaleric acid, or both.

The reductive amination is performed by contacting the formyl-starting compound in water with hydrogen and a molar excess of ammonia in the presence of a ruthenium and at least one group 8-11 metal on carrier, as the catalyst.

The water content in the reaction mixture as described above is at least 10 wt % and more preferably between about 15 and about 60 wt % and most preferably between about 20 and about 50 wt %.

The molar ratio of ammonia and formyl-starting compound in the reductive amination step is preferably between about 3:1 and about 30:1, and more preferably is between about 5:1 and about 20:1.

The temperature is preferably between about 40° C. and about 200° C., and more preferably between about 80° C. and about 160° C.

The process is preferably conducted under pressure. In general, the pressure is equal or greater than the resulting equilibrium pressure of the liquid reaction mixture employed. The pressure is preferably between 0.5 and 10 MPa.

The molar amount of hydrogen is at least equal to the molar quantity of formyl-starting compound. The molar ratio of hydrogen to the formyl-starting compound is preferably between about 1.00 to about 100.

If the starting compound is an alkyl 5-formylvalerate it is preferred that some alcohol, corresponding to this alkyl group is present in the reaction mixture. The concentration of the corresponding alcohol can be between 1 and 15 wt. %, although the alcohol concentration is preferably between 5 and 15 wt % in order to improve the solubility of the alkyl 5-formylvalerate when the concentration of the latter compound is relatively high (>15 wt. %).

The reaction mixture obtained in the process according to the invention comprises ε-caprolactam, 6-aminocaproic acid and 6-aminocaproamide, ammonia, water and some dissolved hydrogen. If the starting compound is an alkyl 5-formylvalerate, a small amount of alkyl 6-aminocaproate and the corresponding alcohol to the alkyl will be present in the reaction mixture. Some oligomers of 6-aminocaproic acid and/or of 6-aminocaproamide may also be formed when the present process is conducted at relatively higher substrate concentrations. These oligomers of e.g., 6-aminocaproic acid, 6-aminocaproamide and the alkyl 6-aminocaproate, are all precursors to ε-caprolactam.

The aqueous mixture from the one-step reductive amination can be used to prepare ε-caprolactam.

The process according to the invention can be performed batch wise or continuously. A large scale commercial process will preferably be performed continuously.

The present invention can be performed continuously in a fixed bed reactor in which the heterogeneous hydrogenation catalyst is present. An advantage of this reactor is that the reactants are easily separated from the hydrogenation catalyst. Another manner of performing the reductive amination is by way of one or more continuously operated well mixed contactors in series in which the hydrogenation catalyst is present as a slurry (slurry reactor). This manner of operation has the advantage that the heat of the reaction can be easily controlled by, for example, a cooled feed or by way of internally placed cooling devices. Examples of specific and suitable slurry reactors are one or multiple staged bubble columns or a gas lift-loop reactor or a continuously stirred tank reactor (CSTR). The slurry-hydrogenation catalyst can be separated from the reaction mixture by for example using hydrocyclones and/or by filtration, for example by cake- or cross-flow filtration.

The catalyst concentration can be suitably selected across a wide concentration range. In a fixed bed reactor the amount of catalyst per reactor volume will be high, while in a slurry-reactor this concentration will, in general be lower. In a continuously operated slurry reactor the weight fraction of catalyst (including the carrier) is typically between about 0.1 and about 30 weight % relative to the total reactor content.

Ammonia, hydrogen, the heterogeneous hydrogenation catalyst and the alcohol (if present) are preferably separated from the reaction mixture obtained in the reductive amination prior to the cyclization step to ε-caprolactam. Hydrogen and part of the ammonia can advantageously be separated from this reaction mixture by reducing the pressure and performing a gas/liquid separation. An example of such an operation is a flash operation performed at between ambient about pressure and about 0.5 MPa. Advantageously, the hydrogen and ammonia can be recycled to the reductive amination step.

Subsequent to the reductive amination, the ε-caprolactam precursors present in the aqueous mixture can be further reacted to ε-caprolactam as for example described in PCT/NL98/00083.

EXAMPLE I 1 gram of 5 wt. % ruthenium on zirconium oxide (BET surface area 86 $m^2$/g) was introduced in a 100 ml autoclave and 5.8 mg Rh(CO)$_2$AcAc was added. The catalyst was reduced in 57 gram of water at 150° C. at 5.0 MPa hydrogen during 1 hour. After addition of 23.1 gram ammonia, the temperature was brought to 100° C. and the pressure to 5.0 MPa. Subsequently 2.8 gram methyl-5-formylvalerate and 1.5 gram methanol were added. The calculated first order reaction coefficient was $126*10^{-4}$ per second. The total yield of ε-caprolactam and ε-caprolactam precursors was 98%.

Comparative Experiment A 1 gram of 5 wt. % ruthenium on gamma-alumina was introduced in a 100 ml autoclave. The catalyst was reduced in 57 gram of water at 150° C. at 5.0 MPa hydrogen during 1 hour. After addition of 24.5 gram ammonia, the temperature was brought to 100° C. and the pressure to 5.0 MPa. Subsequently 2.8 gram methyl-5-formylvalerate and 1.5 gram methanol were added. The calculated first order reaction coefficient was $43*10^{-4}$ per second. The total yield of ϵ-caprolactam and ϵ-caprolactam precursors was 83%.

Comparative Experiment B 1.12 gram of Raney-nickel and 78.5 gram of water were introduced in a 180 ml autoclave. After addition of 13.7 gram ammonia, the temperature was brought to 100° C. and the pressure to 4.0 MPa. Subsequently 10.1 gram methyl-5-formylvalerate was added. The calculated first order reaction coefficient was $62*10^{-4}$ per second. The total yield of ϵ-caprolactam and ϵ-caprolactam precursors was 85%.

EXAMPLE II 0.16 gram of 5 wt. % ruthenium on titanium oxide (BET surface area 55 m$^2$/g) was introduced in a 100 ml autoclave and 0.77 mg of Ni(NO$_3$).6H$_2$O was added. The catalyst was reduced in 56 gram of water at 150° C. at 5.0 MPa hydrogen during 1 hour. After addition of 23.1 gram ammonia, the temperature was brought to 100° C. and the pressure to 5.0 MPa. Subsequently 2.8 gram methyl-5-formylvalerate and 1.5 gram methanol were added. The calculated first order reaction coefficient was $249*10^{-4}$ per second. The total yield of ϵ-caprolactam and ϵ-caprolactam precursors was 90%.

EXAMPLE III 0.16 gram of 5 wt % ruthenium on titanium oxide (BET surface area 55 m$^2$/g) was introduced in a 100 ml autoclave and 7.8 mg of Ni(NO$_3$).6H$_2$O was added. The catalyst was reduced in 56 gram of water at 150° C. at 5.0 MPa hydrogen during 1 hour. After addition of 23.1 gram ammonia, the temperature was brought to 100° C. and the pressure to 5.0 MPa. Subsequently 2.6 gram methyl-5-formylvalerate and 1.4 gram methanol were added. The calculated first order reaction coefficient was $369*10^{-4}$ per second. The total yield of ϵ-caprolactam and ϵ-caprolactam precursors was 99.8%.

EXAMPLE IV 0.16 gram of 5 wt % ruthenium on titanium oxide (BET surface area 55 m$^2$/g) was introduced in a 100 ml autoclave and 2.4 mg of Ni(NO$_3$).6H$_2$O was added. The catalyst was reduced in 56 gram of water at 150° C. at 5.0 MPa hydrogen during 1 hour. After addition of 23.1 gram ammonia, the temperature was brought to 100° C. and the pressure to 5.0 MPa. Subsequently 2.7 gram methyl-5-formylvalerate and 1.5 gram methanol were added. The calculated first order reaction coefficient was $257*10^{-4}$ per second. The total yield of ϵ-caprolactam and ϵ-caprolactam precursors was 89%.

EXAMPLE V 132 grams of 5 wt % ruthenium and 0.3 wt % nickel on titanium oxide (BET surface area 55 m$^2$/g) were introduced in a 1.5 liter Hastelloy-C reactor. After the addition of water, the catalyst was pre-reduced at 140° C. during 12 hours. Subsequently, an aqueous stream consisting of 25 wt % methyl 5-formylvalerate, 40 wt % ammonia and 7 wt % methanol in water, was fed continuously to the reactor at a rate of 1095 grams/hour. The reactor was kept at a constant pressure of 4.0 MPa by a hydrogen stream of 7.5 grams per hour. The reaction was performed at 140° C. During 154 hours the effluent which continuously left the reactor was analyzed at regular intervals. A constant yield of desired products, i.e. ϵ-caprolactam and caprolactam precursors, of 99.8% was obtained.

Comparative Experiment C

Example V was repeated but with 212 grams of 5 wt. % ruthenium on alumina (d$_{50}$: 74 μm), 30 wt. % ammonia in the feed and a total pressure of 3.0 MPa.

The yield of desired products was 98%. However, after 200 hours the d$_{50}$ was 1 μm, making this catalyst not suitable for use in a large scale process.

Comparative Experiment D 50 grams of Raney-Nickel were introduced in a 1 liter Hastelloy-C reactor. An aqueous stream consisting of 5 wt. % methyl-5-formylvalerate and 20 wt. % ammonia in water, was fed continuously to the reactor at a rate of 875 grams/hour. The reactor was kept at a constant pressure of 1.5 MPa by a hydrogen stream of 10 grams per hour. The reaction was performed at 100° C.

The yield of desired products was 96% during the first 6 hours. However, within 18 hours the yield decreased to 48% and only 21 grams of catalyst was left over in the reactor. This catalyst loss makes this catalyst not suitable for a large scale process.

What we claim is:

1. A process for preparing an aqueous mixture of ϵ-caprolactam and 6-aminocaproic acid and/or 6-aminocaproamide by reductively aminating 5-formylvaleric acid and/or an alkyl 5-formylvalerate in water with hydrogen and an excess of ammonia in the presence of ruthenium on carrier as a catalyst, wherein the carrier is titanium oxide, zirconium oxide, graphite or carbon and the catalyst also contains at least one further group 8-11, or a compound of these metals.

2. A process according to claim 1, wherein the amount of group 8-11 metal (as metal) in the catalyst (metals plus carrier) is between 0.05 and 30 wt. %.

3. A process according to claim 2, wherein the amount of group 8-11 metal (as metal) in the catalyst (metals plus carrier) is between 0.1 and 10 wt. %.

4. A process according to claim 1, wherein the amount of ruthenium (as metal) in the catalyst is between 0.1 and 10 wt %.

5. A process according to claim 1, wherein the carrier is titanium oxide or zirconium oxide.

6. A process according to claim 1, wherein the particle size of the catalyst is between 10 and 100 μm and the catalyst is present as a slurry in the reaction mixture.

7. A process according to claim 1, wherein the particle size of the catalyst is between 0.001 and 0.05 m and the step is performed in a fixed bed reactor.

8. A process according to claim 1, wherein the catalyst has a BET surface area of between 30 and 100 m$^2$/g.

9. A process according to claim 1, wherein said process comprises reductively aminating said alkyl 5-formylvalerate which is a C$_1$–C$_6$ alkyl 5-formylvalerate.

10. A process for preparing ϵ-caprolactam comprising reacting an aqueous mixture obtained according to the process of claim 1 to ϵ-caprolactam.

11. A process according to claim 5, wherein the at least one further group 8-11 metal includes at least one of rhodium or nickel.

12. A process according to claim 5, wherein the at least one further group 8-11 metal is rhodium.

13. A process according to claim 5, wherein the at least one further group 8-11 metal is nickel.

* * * * *

UNITED STATES PATENT AND TRADEMARK OFFICE
CERTIFICATE OF CORRECTION

PATENT NO.    : 6,452,002 B2
DATED         : September 17, 2002
INVENTOR(S)   : Pestman et al.

It is certified that error appears in the above-identified patent and that said Letters Patent is hereby corrected as shown below:

<u>Title page,</u>
Item [63], Related U.S. Application Data information, please change the filing date of Provisional Application No. 60/100,404 to read -- Sep. 15, 1998 --.

Signed and Sealed this

First Day of April, 2003

JAMES E. ROGAN
*Director of the United States Patent and Trademark Office*